(12) United States Patent
Weber et al.

(10) Patent No.: US 7,674,238 B2
(45) Date of Patent: Mar. 9, 2010

(54) METHODS AND APPARATUS FOR EMBOLI REMOVAL

(75) Inventors: Jan Weber, Maple Grove, MN (US); Tracee E. J. Eidenschink, Wayzata, MN (US); David J. Sogard, Edina, MN (US); Joel M. WasDyke, Eden Prairie, MN (US); Thomas J. Holman, Princeton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 516 days.

(21) Appl. No.: 11/021,381

(22) Filed: Dec. 23, 2004

(65) Prior Publication Data

US 2006/0142796 A1    Jun. 29, 2006

(51) Int. Cl.
*A61M 29/00* (2006.01)
(52) U.S. Cl. .......................................................... 604/8
(58) Field of Classification Search ................. 606/200, 606/127; 604/5, 327–328, 403, 405–406, 604/408, 6.09, 8, 540
See application file for complete search history.

(56) References Cited

U.S. PATENT DOCUMENTS

| | | | |
|---|---|---|---|
| 5,549,626 A * | 8/1996 | Miller et al. ................. 606/200 |
| 6,048,331 A * | 4/2000 | Tsugita et al. ........... 604/102.03 |
| 6,371,935 B1 | 4/2002 | Macoviak et al. |
| 6,395,014 B1 | 5/2002 | Macoviak et al. |
| 6,406,471 B1 * | 6/2002 | Jang et al. .................... 604/540 |
| 6,499,487 B1 | 12/2002 | McKenzie et al. |
| 6,508,826 B2 | 1/2003 | Murphy et al. |
| 6,540,712 B1 * | 4/2003 | Parodi et al. ................ 604/6.14 |
| 6,623,507 B2 | 9/2003 | Saleh |
| 6,652,555 B1 | 11/2003 | VanTassel et al. |
| 6,652,556 B1 | 11/2003 | VanTassel et al. |
| 6,673,089 B1 | 1/2004 | Yassour et al. |
| 6,682,505 B2 | 1/2004 | Bates et al. |
| 6,689,084 B2 | 2/2004 | Kaganov et al. |
| 6,689,150 B1 | 2/2004 | VanTassel et al. |
| 6,692,513 B2 | 2/2004 | Streeter et al. |
| 6,695,864 B2 | 2/2004 | Macoviak et al. |
| 6,695,865 B2 | 2/2004 | Boyle et al. |
| 6,712,834 B2 | 3/2004 | Yassour et al. |
| 6,723,085 B2 | 4/2004 | Jang et al. |
| 6,730,108 B2 | 5/2004 | VanTassel et al. |
| 6,740,112 B2 | 5/2004 | Yodfat et al. |
| 6,743,246 B1 | 6/2004 | Maahs |
| 2001/0049486 A1 * | 12/2001 | Evans et al. ................. 604/4.01 |
| 2002/0045932 A1 * | 4/2002 | Isracl ......................... 623/1.15 |
| 2002/0107479 A1 | 8/2002 | Bates et al. |

FOREIGN PATENT DOCUMENTS

| | | |
|---|---|---|
| WO | 9945835 A2 | 9/1999 |
| WO | 0076390 A2 | 12/2000 |
| WO | 2005027751 A1 | 3/2005 |

* cited by examiner

*Primary Examiner*—(Jackie) Tan-Uyen T. Ho
*Assistant Examiner*—Melanie Tyson
(74) *Attorney, Agent, or Firm*—Crompton, Seager & Tufte LLC (57) ABSTRACT

Improved methods and apparatus for capturing emboli and subsequently removing or immobilizing the captured emboli are described. Emboli can be captured within a blood vessel and can be withdrawn to a position exterior to the blood vessel. Some filters can remain within a blood vessel yet direct emboli to a position exterior to the blood vessel.

4 Claims, 8 Drawing Sheets

METHODS AND APPARATUS FOR EMBOLI REMOVAL

TECHNICAL FIELD

The invention relates generally to capturing intravascular emboli.

BACKGROUND

Heart and vascular disease are major problems in the United Sates and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques such as PTA and PTCA typically involve the use of a balloon catheter. The balloon catheter is advanced over a guidewire such that the balloon is positioned adjacent a stenotic lesion. The balloon is then inflated, and the restriction in the vessel is opened. During an atherectomy procedure, the stenotic lesion may be mechanically or otherwise cut away from the blood vessel wall using an atherectomy catheter.

During procedures such as angioplasty and atherectomy procedures, as well during other operations and even as a result of natural events, embolic debris can be separated from the wall of the blood vessel. If this debris enters the circulatory system, it can block other vascular regions including the neural and pulmonary vasculature. During angioplasty procedures, stenotic debris may also break loose due to manipulation of the blood vessel.

Because of this debris, a number of devices such as intravascular filters have been developed to filter out debris. A need remains for improved methods of capturing and removing intravascular emboli.

SUMMARY

The present invention is directed to improved methods and techniques for capturing emboli and subsequently removing or immobilizing the captured emboli. The present invention is also directed to a filter that is adapted to capture emboli and direct emboli away from the vessel in which the filter is deployed.

Accordingly, an example embodiment of the invention can be found in a method of removing emboli from a blood vessel that has a vessel wall that defines an interior of the blood vessel. Blood can flow through the interior of the blood vessel. A pocket is provided that is exterior to the blood vessel but in fluid communication with the interior of the blood vessel. A portion of the blood flowing through the interior of the blood vessel may be diverted such that emboli within the blood flow are carried into the pocket.

Another example embodiment of the invention can be found in a method of removing emboli from a blood vessel that includes a lumen. A filter having an open end and a tapered end may be positioned within the lumen such that the open end is positioned upstream and the tapered end is positioned downstream. The tapered end of the filter may be in fluid communication with a tube leading to a position exterior to the blood vessel. Emboli may be captured within the filter and can be passed through the tube and thus can be passed to a position exterior to the blood vessel.

Another example embodiment of the invention can be found in an intravascular filter that includes an open end that is adapted to fit within a blood vessel, a tapered end and a tube that is in fluid communication with the tapered end. A valve may be positioned at the tapered end.

Another example embodiment of the invention can be found in a method of removing emboli from a blood vessel. The blood vessel includes a vessel wall that defines an interior of the blood vessel having blood flowing therethrough. An external port can be provided that is exterior to the blood vessel but in fluid communication with the interior of the blood vessel. A one-way valve that permits flow from the interior of the blood vessel into the external port but does not permit flow from the external port to the interior of the blood vessel can be provided. A temporal blood pressure increase may permit blood flow through the one-way valve such that emboli within the blood flow are carried into the external portion.

Another example embodiment of the invention can be found in a method of removing emboli from a vein that is transporting blood back from a patient's leg. A filter can be positioned within the vein. Emboli can be captured within the filter and can be shunted into an artery that carries blood into the leg. As a result, the captured emboli are harmlessly ensnared within the patient's feet.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value, i.e., having the same function or result. In many instances, the term "about" may include numbers that are rounded to the nearest significant figure.

As used in this specification and in the appended claims, the singular forms "a", "an", and "the" include plural referents unless the content clearly dictates otherwise. As used in this specification and in the appended claims, the term "or" is generally employed in its sense including "and/or" unless the content clearly dictates otherwise.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
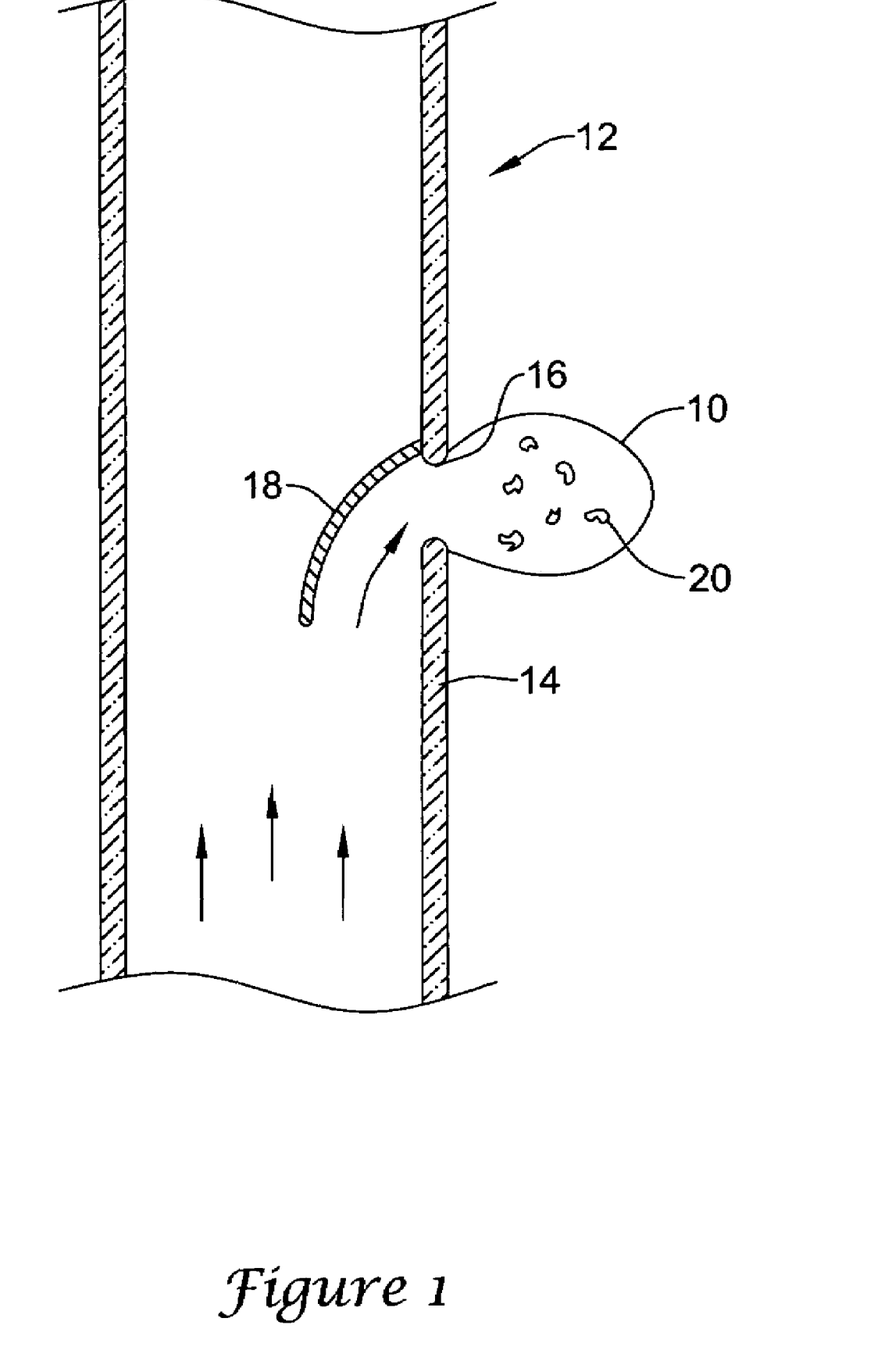
FIG. 1 is a schematic illustration of a method in accordance with an embodiment of the invention.

Turning now to FIG. 1, a pocket 10 has been formed proximate to a blood vessel 12 having a vessel wall 14. In some embodiments, an aperture 16 can be formed within the vessel wall 14 using any suitable technique. In the illustrated embodiment, the pocket 10 can be formed from a piece of any suitable material that can be passed through the blood vessel 12 and pushed at least partially through the aperture 16 to form the pocket 10. In some cases, the pocket 10 may be formed from material that is inserted into aperture 16 from a position exterior to the vessel wall 14.

In some instances, the pocket 10 may be formed from any suitable metallic, polymeric, biological or even autogenous vascular material, i.e. material grafted from another location with the patient's vasculature. The piece of material used to form the pocket 10 can be any suitable fluid-tight mesh or solid polymeric layer. In other embodiments, the pocket 10 can be rigidly formed and can include a narrowed portion adapted to fit through the aperture 16.

As illustrated, a diverter 18 is positioned near to but just downstream of the aperture 16. The diverter 18 functions to divert at least a portion of blood flow into the pocket 10 such that at least some of the emboli that may be present within the blood flow are captured within the pocket 10 as captured emboli 20. The diverter 18 may be formed of any suitable metallic, polymeric, biological or even autogenous vascular material. The diverter 18 can be positioned within the blood vessel 12 by inserting the diverter 18 through the vessel wall 14 from a position exterior to the blood vessel 12. In some embodiments, the diverter 18 can be formed by a portion of a filter positioned within the blood vessel 12. In some cases, the diverter 18 can be stationary while in other instances the diverter 18 may be configured to move back and forth, much like an automotive windshield wiper, to better direct emboli into the pocket 10.

Figure 2:
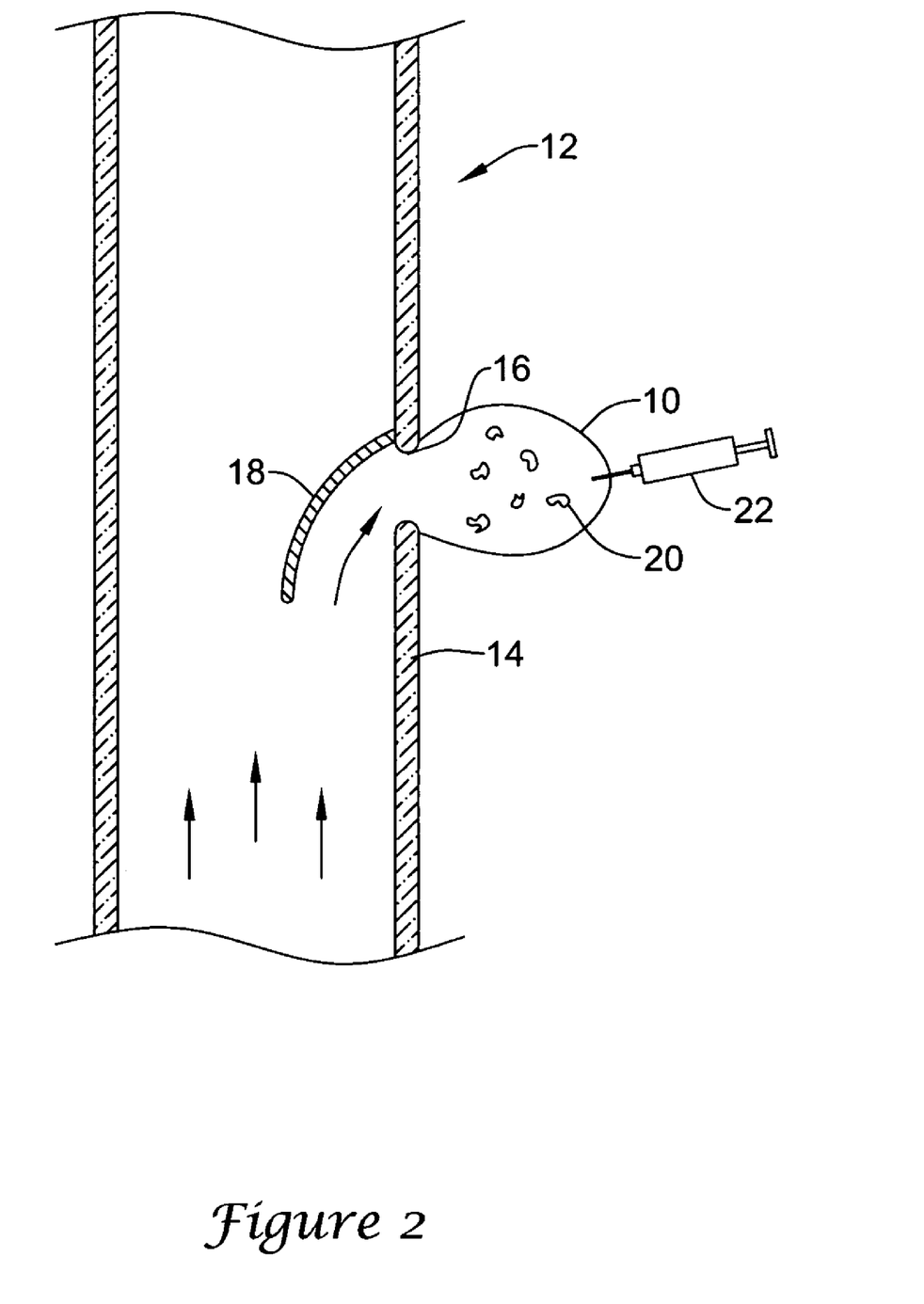
FIG. 2 is a schematic illustration of a method in accordance with an embodiment of the invention.

Eventually, the pocket 10 may become full or at least substantially full with captured emboli 20. In FIG. 2, a syringe 22 is inserted into the pocket 10 and is used to remove the captured emboli 20 from the pocket 10. In other embodiments, any suitable source of suction, such as an aspiration needle fluidly connected to a vacuum pump, can be used. In some instances, the syringe 22 may be used to inject a thrombolytic agent to dissolve or otherwise lyse the captured emboli 20.

Figure 3:
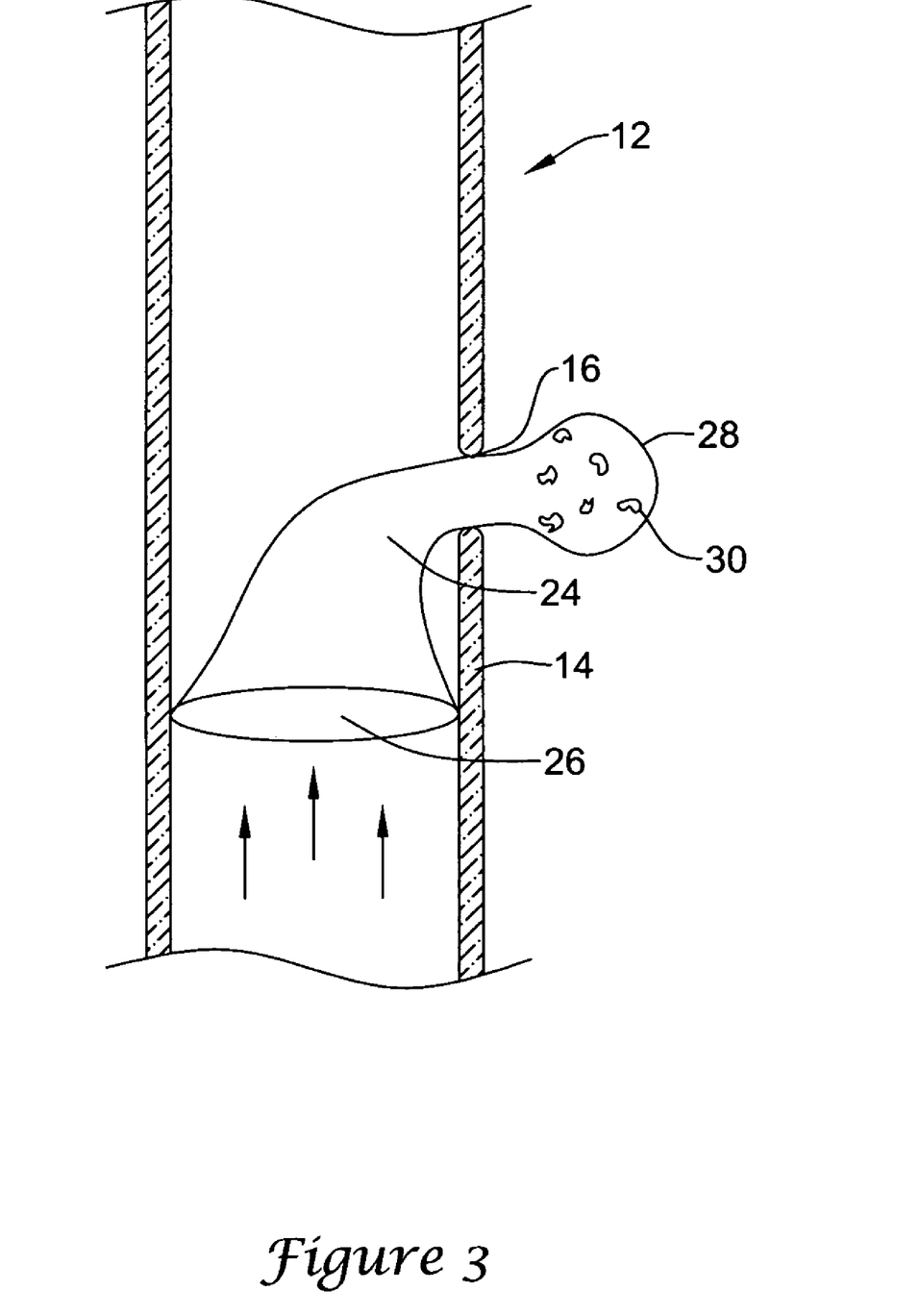
FIG. 3 is a schematic illustration of a method in accordance with an embodiment of the invention.

FIG. 3 illustrates an embodiment in which the diverter and pocket are integrally formed. Blood vessel 12 includes a vessel wall 14 having an aperture 16, as before. An assembly 24 is positioned within the blood vessel 12 such that a filter portion 26 is located within blood vessel 12 and thus is subjected to blood flow while a pocket portion 28 extends through the aperture 16 and exterior to the blood vessel 12. Part or all of the assembly 24 may be coated with a material designed to prevent clotting and perhaps to stimulate endothelial cell growth in an interior of the pocket portion 28. Smooth muscle cell growth near the aperture 16 may be prevented by a suitable coating. An exemplary coating includes a combination of SIBS and PACLITAXEL™. SIBS, or poly(styrene-b-isobutylene-b-styrene), is commercially available from Boston Scientific Corporation under the tradename TRANSLUTE™. PACLITAXEL™ is a plant-derived antiproliferative agent.

In some instances, the assembly 24 may be advanced through the blood vessel 12 and can be advanced through the aperture 16 to reach its operational position, as indicated. In some cases, however, the assembly 24 may be provided from exterior to the blood vessel 12. The pocket portion 28 remaining outside the blood vessel 12 may be flood sealed. The filter portion 26 located within the blood vessel 12 may include self-unfolding hooks (not illustrated) to assure that the filter portion 26 is properly positioned.

Blood flowing through the blood vessel 12 will encounter the filter portion 26. Blood will pass through, but at least a portion of any emboli that may be present within the blood flow will be captured by the filter portion 26. The filter portion 26 can be formed of any suitable filter mesh such that blood can pass through but potentially harmful emboli are captured. The captured emboli 30 pass into the pocket portion 28 and await removal in any suitable manner. Suction such as that described with respect to FIG. 2 may be used to remove the captured emboli 30 from the pocket portion 28.

Figure 4:
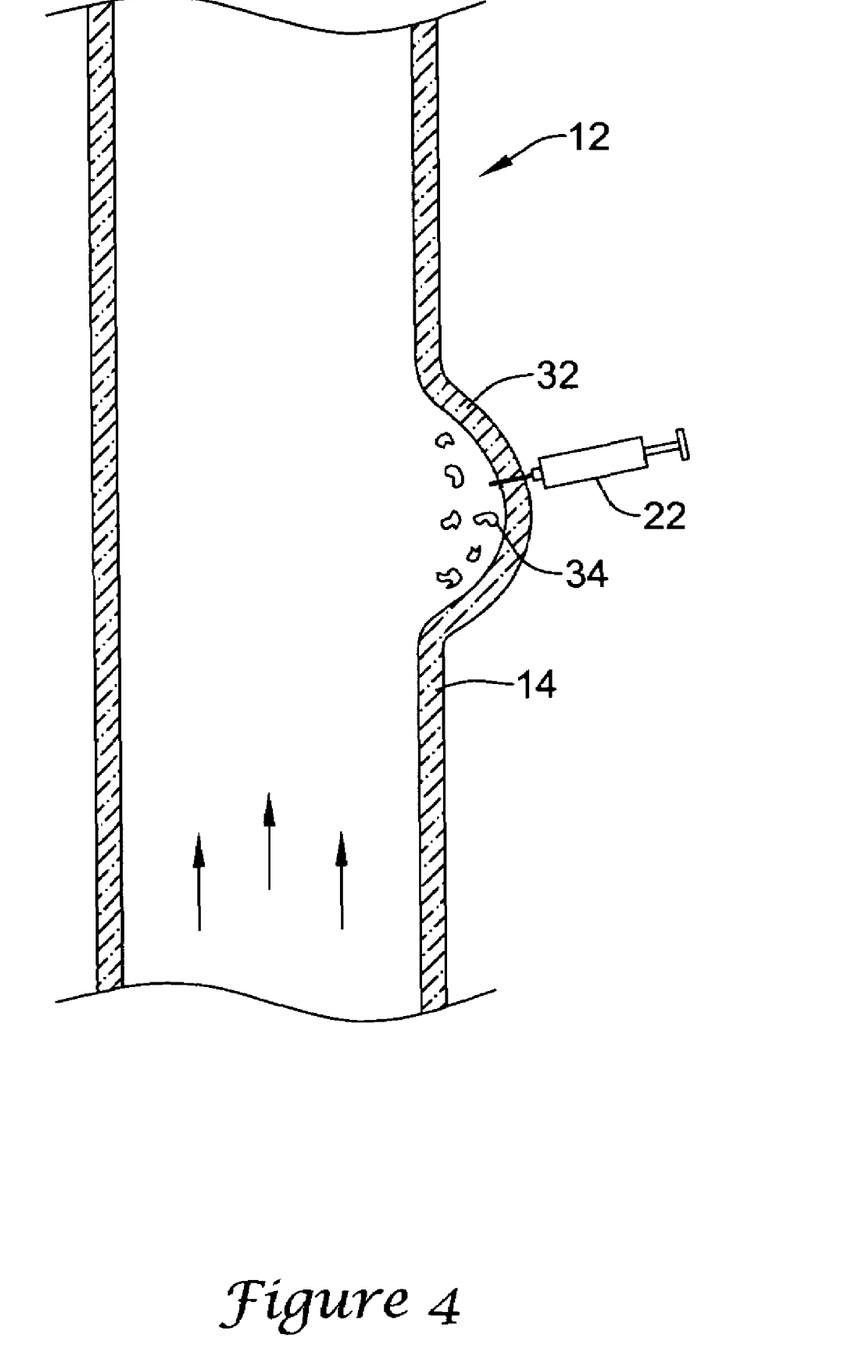
FIG. 4 is a schematic illustration of a method in accordance with an embodiment of the invention.

Turning now to FIG. 4, another embodiment is illustrated. Rather than inserting an artificial pocket as previously discussed, a pocket 32 is formed by weakening a portion of the blood vessel wall 14. This can be done in any suitable manner, such as abrading away a portion of the vessel wall 14, using a balloon catheter to stretch a portion of the vessel wall 14, or perhaps chemically weakening a portion of the vessel wall 14.

Much as discussed with respect to FIGS. 1 and 2, emboli 34 can collect within the pocket 32. Once the pocket 32 becomes full, at least a portion of the captured emboli 34 can be removed using a syringe 22 or any other suitable suction technique. In some cases, the captured emboli 34 can remain within the pocket 32. In some instances, a thrombolytic agent may be injected into the pocket 32 to dissolve or otherwise lyse the captured emboli 34.

Figure 5:
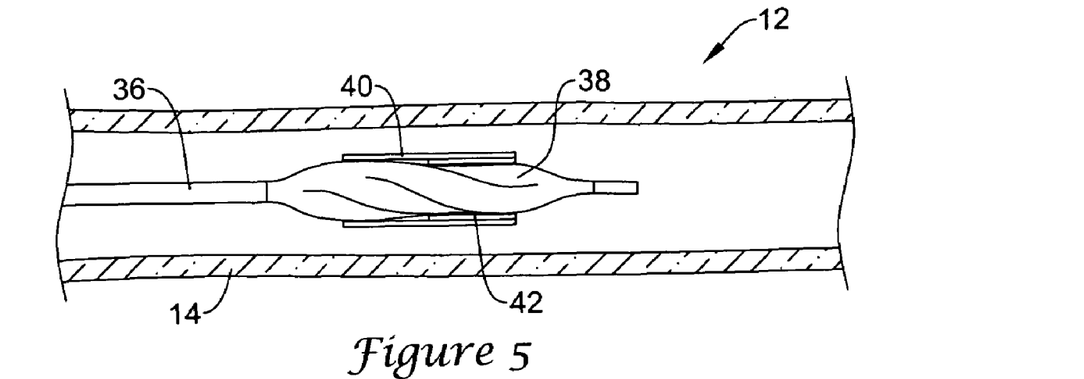
FIG. 5 is a schematic illustration of a method in accordance with an embodiment of the invention.
Figure 6:
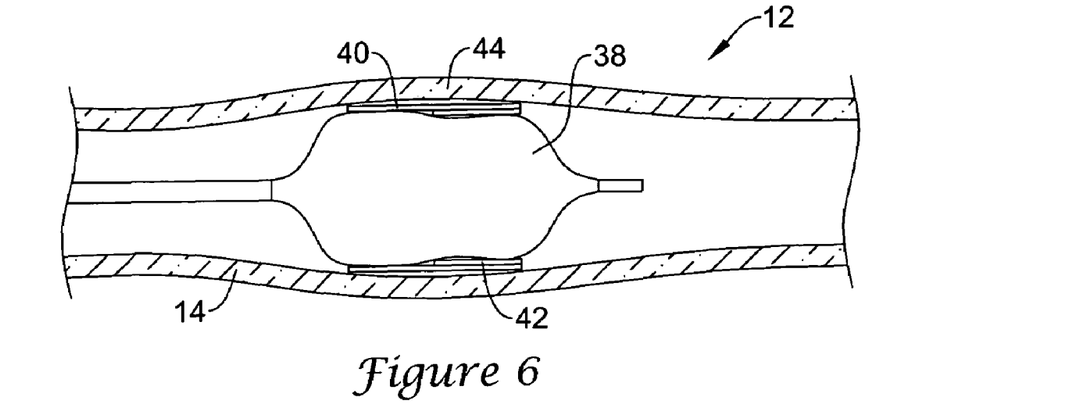
FIG. 6 is a schematic illustration of a method in accordance with an embodiment of the invention.
Figure 7:
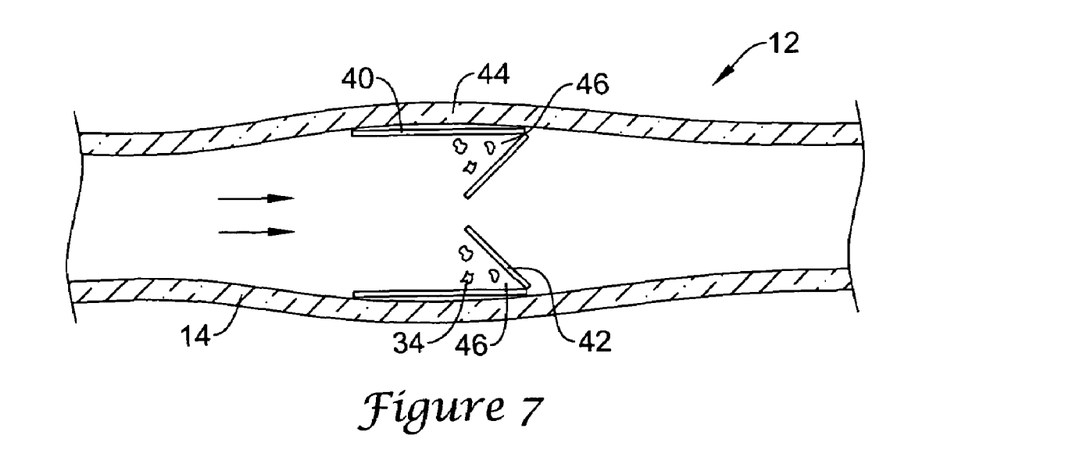
FIG. 7 is a schematic illustration of a method in accordance with an embodiment of the invention.

FIGS. 5-7 illustrate a particular method of forming a collection area. In FIG. 5, a balloon catheter 36 including a balloon 38 is positioned within the blood vessel 12. A stent 40 is positioned over the balloon 38 as is known in the art. The stent 40 may be formed of any suitable material such as stainless steel. The stent 40 may include inner wires 42 that can be formed of any suitable material such as nitinol. In FIG. 6, the balloon 38 has been over-inflated, thereby expanding a portion 44 of the vessel wall 14.

Once the balloon 38 has been de-inflated, as shown in FIG. 7, the stent 40 remains in position while the inner wires 42 are allowed to fold inwards to form collection areas 46. While not expressly illustrated, a reinforcing layer or member may be placed either interior to the portion 44 or exterior to the portion 44. The reinforcing layer may prevent additional expansion of the portion 44. In some cases, the reinforcing layer may prevent portion 44 from collapsing, or recoiling. Emboli 34 that collect within the collection areas 46 may be removed in any suitable manner such as discussed with respect to FIGS. 2, 3 and 4.

Figure 8:
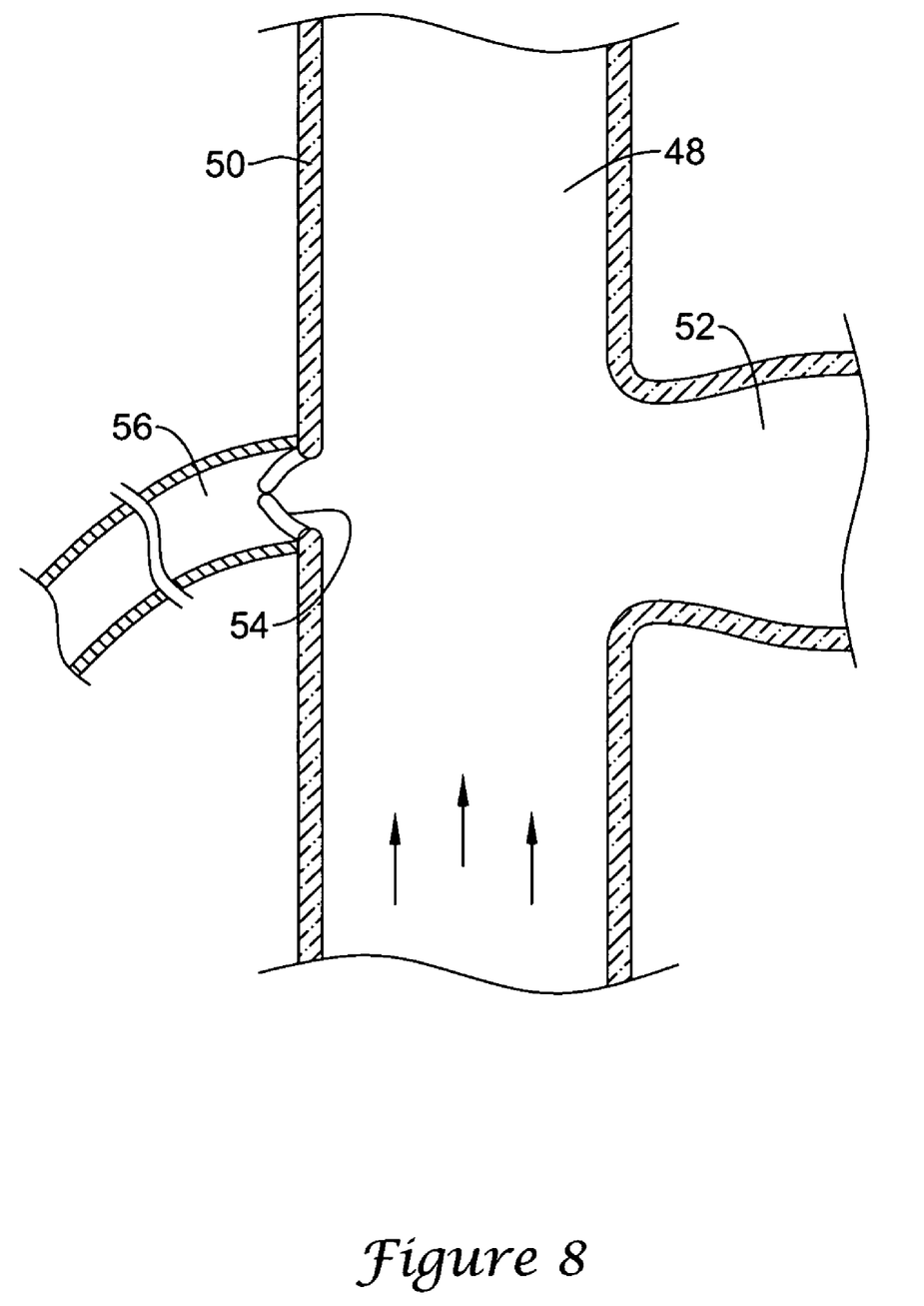
FIG. 8 is a schematic illustration of a method in accordance with an embodiment of the invention.

FIG. 8 shows a particular embodiment having usefulness closer to a patient's heart. A blood vessel 48 has a vessel wall 50. Blood vessel 48 is positioned proximate a valve 52 that controls blood flow between the right atrium and the right ventricle. A one-way valve 54 is positioned within the vessel wall 50 such that the one-way valve 54 is in communication with an external port 56. The external port 56 can lead to a collection point within the patient or the external port 56 can lead to a position external to the patient. When the valve 52 closes, the resulting temporal increase in blood pressure causes blood to flow towards the one-way valve 54. As a result, emboli present within the blood flow may be carried through the one-way valve 54 and into the external port 56.

Figure 9:
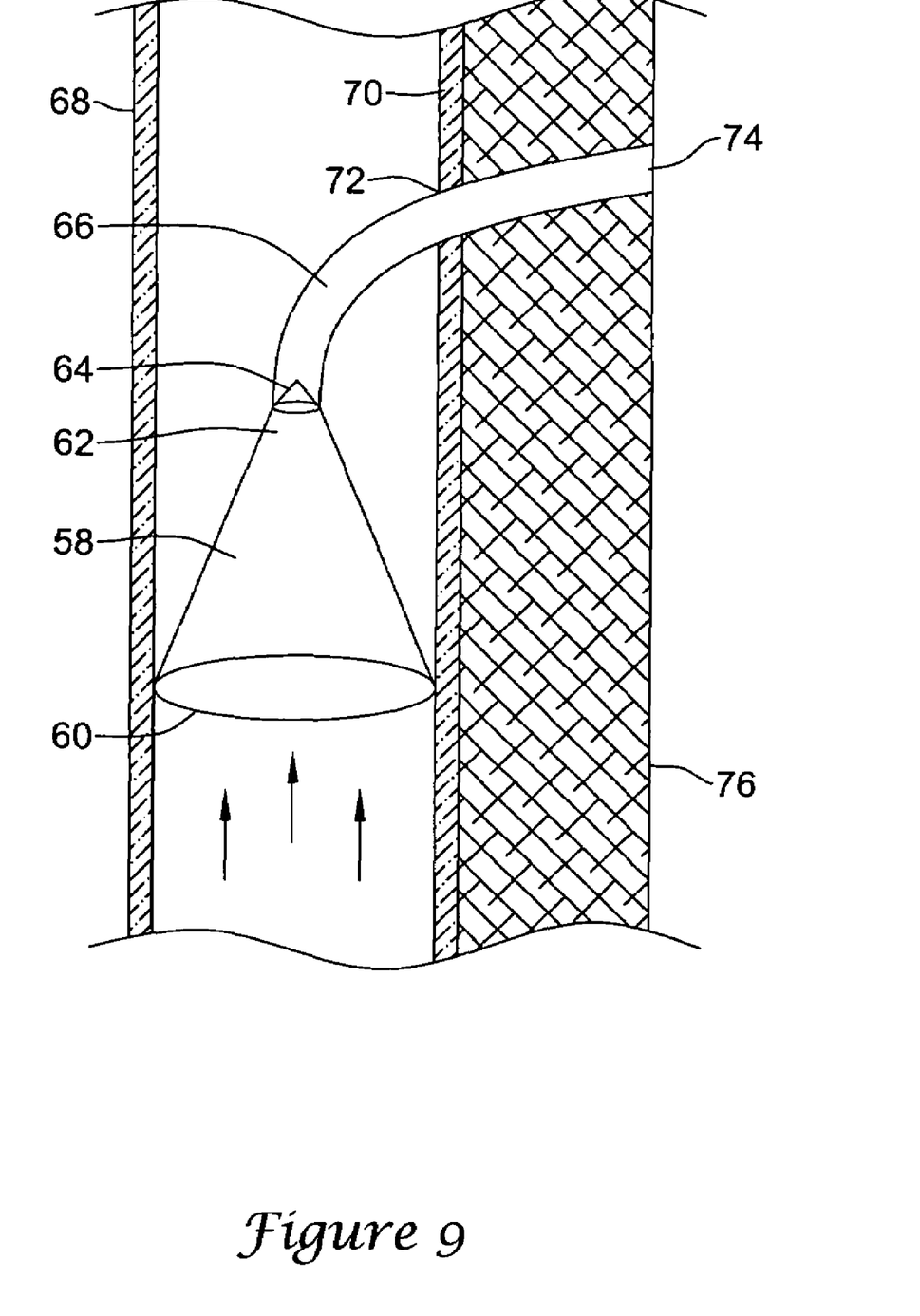
FIG. 9 is a schematic illustration of a method in accordance with an embodiment of the invention.

Turning now to FIG. 9, another embodiment of the invention is illustrated. A filter 58 includes an open end 60 and a tapered end 62. A valve 64 may be positioned at the tapered end 62 that is in communication with a tube 66. The filter 64 is seen within a blood vessel 68 having a vessel wall 70. The tube 66 can extend through an aperture 72 in the vessel wall 70 and can extend to a valve 74 that is positioned proximate a portion 76 of the patient's skin.

At least a portion of any emboli present within the blood flow will be captured by the filter 58 and can pass through the valve 64 into the tube 66. As a result, the captured emboli can be removed from the patient through valve 74 without removing the filter 58 from the patient.

Figure 10:
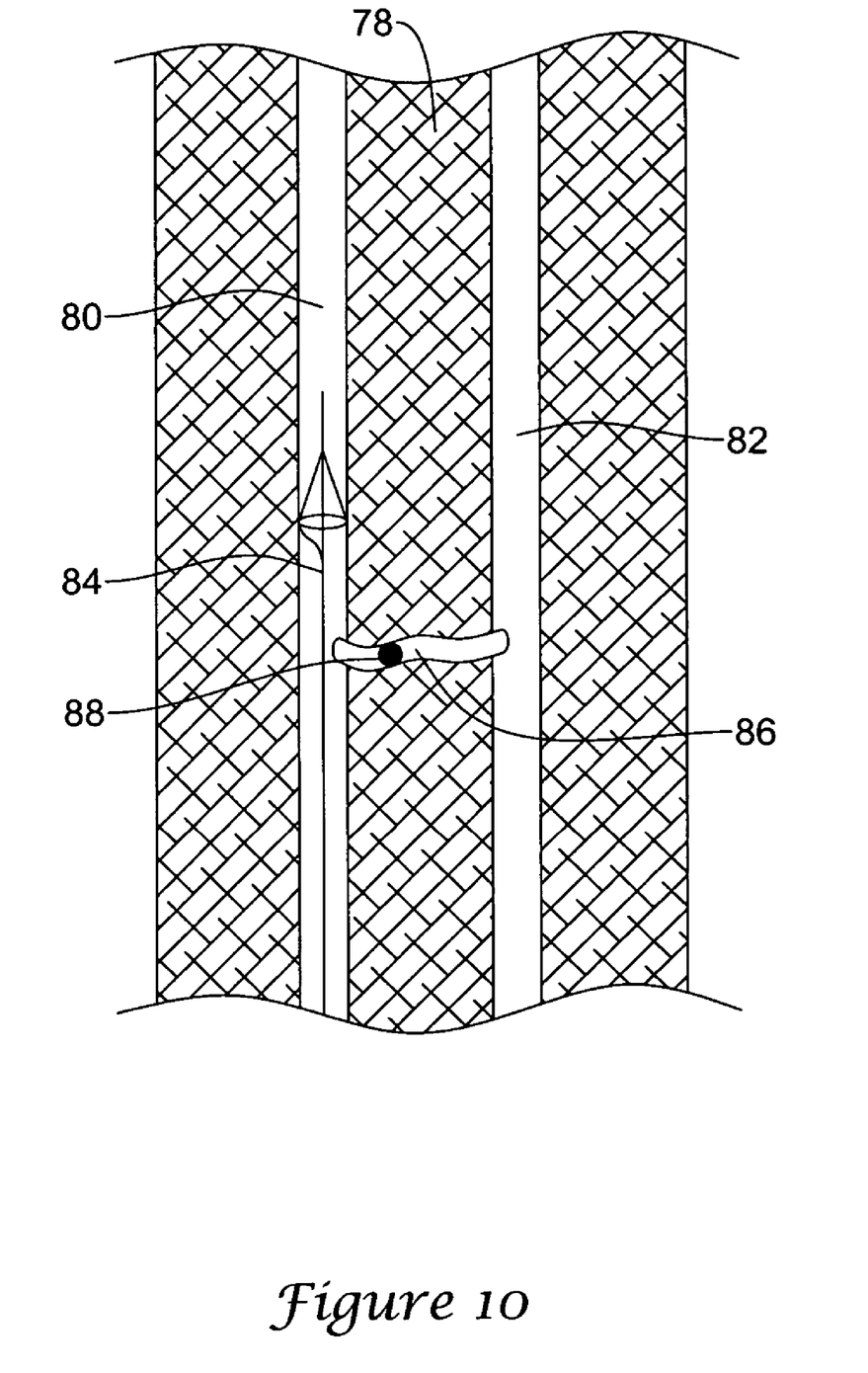
FIG. 10 is a schematic illustration of a method in accordance with an embodiment of the invention.

FIG. 10 illustrates a method of capturing and disposing of emboli present in a patient's leg 78. The leg 78 includes a vein 80 carrying spent blood towards the heart and lungs and an artery 82 that carries replenished blood back into the leg 78. Emboli traveling within the vein 80 can be captured by a filter 84. The filter 84 can be any suitable intravascular filter as known in the art. A shunt 86 can be positioned between the vein 80 and the artery 82 such that any emboli captured within the filter 84 can be directed through the shunt 86 and into the artery 82.

In some instances, the blood pressure within the artery 82 may be higher than the blood pressure within the vein 80. Consequently, a collection ball 88 may be disposed along the shunt 86. A first one-way valve (not illustrated) within the collection ball 88 permits blood to exit the vein 80 and enter a collection volume within the collection ball 88. A second one-way valve within the collection ball 88 permits blood to exit the collection volume and enter the artery 82. The collection ball 88 may be disposed relatively close to the patient's skin so that squeezing or depressing the collection ball 88 can activate the first and second one-way valves. Captured emboli are carried downward through the artery 82 and can harmlessly collect in the patient's feet.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

We claim:

1. A method of removing emboli from a blood vessel, the blood vessel including a vessel wall defining an interior of the blood vessel with blood flowing therethrough, the method comprising steps of:
   forming an aperture through the vessel wall;
   providing a pocket;
   positioning the pocket such that the pocket extends through the aperture at least in part to a position exterior to the blood vessel and in fluid communication with the interior of the blood vessel;
   providing a diverter positioned within the interior of the blood vessel;
   diverting a portion of the blood flow such that emboli within the blood flow are carried into the pocket; and
   removing the emboli from the pocket using a syringe inserted into the pocket.

2. The method of claim 1, wherein providing a pocket comprises inserting an artificial pocket at least partially through the aperture.

3. The method of claim 2, wherein inserting the artificial pocket at least partially through the aperture comprises inserting the artificial pocket at least partially through the aperture from the interior of the blood vessel.

4. The method of claim 1, wherein diverting a portion of the blood flow comprises moving the diverter back and forth to better direct emboli into the pocket.

* * * * *